United States Patent

Rentzea et al.

[11] 4,430,336
[45] Feb. 7, 1984

[54] N-SUBSTITUTED 2-METHYLNAPHTHYLAMIDES, THEIR PREPARATION AND FUNGICIDES CONTAINING THESE COMPOUNDS

[75] Inventors: Costin Rentzea, Heidelberg; Bernd Zeeh, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 208,033

[22] Filed: Nov. 18, 1980

[30] Foreign Application Priority Data

Dec. 4, 1979 [DE] Fed. Rep. of Germany ....... 2948704

[51] Int. Cl.³ .................... A01N 43/80; C07D 261/14
[52] U.S. Cl. .................................... 424/272; 548/240;
548/243; 548/245; 548/246; 548/248; 548/249;
548/262; 548/378; 424/269; 424/278; 560/129;
564/189; 564/204; 564/209; 564/215; 549/448;
549/487
[58] Field of Search ............... 548/240, 243, 245, 246,
548/248, 249; 71/118; 424/272

[56] References Cited

U.S. PATENT DOCUMENTS 2,412,510 10/1946 Jones ................................. 71/118
3,272,844 9/1966 Easton et al. ..................... 71/118
4,098,895 7/1978 Hubele et al. .................... 424/269
4,221,584 9/1980 Zimon ............................... 71/88

FOREIGN PATENT DOCUMENTS 18510 11/1980 European Pat. Off. ............. 71/118
1003221 2/1957 Fed. Rep. of Germany .
1768435 9/1971 Fed. Rep. of Germany .
2409011 9/1974 Fed. Rep. of Germany .
1177129 12/1967 United Kingdom ............... 548/240
2008576 6/1979 United Kingdom .

Primary Examiner—Donald G. Daus
Assistant Examiner—G. Hendricks
Attorney, Agent, or Firm—Keil & Witherspoon

[57] ABSTRACT

N-Substituted 2-methylnaphthylamides of the general formula

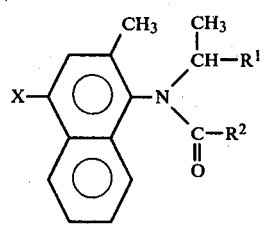

where
$R^1$ is

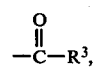

$R^3$ being hydrogen or alkoxy, or $R^1$ is

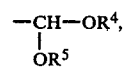

$R^4$ and $R^5$ being unsubstituted or substituted alkyl, or $R^4$ and $R^5$ together forming a heterocyclic ring which contains two oxygen atoms and is unsubstituted or substituted by alkyl or aryl,
$R^2$ is alkyl which is unsubstituted or substituted by halogen, alkoxy, imidazolyl, pyrazolyl or oxo (=O), or is alkenyl, alkynyl, cycloalkenyl or alkoxy, or substituted or unsubstituted phenyl, or substituted or unsubstituted hetaryl and
X is hydrogen, methyl or halogen, fungicides containing these compounds, and processes for the preparation of the compounds.

4 Claims, No Drawings

N-SUBSTITUTED 2-METHYLNAPHTHYLAMIDES, THEIR PREPARATION AND FUNGICIDES CONTAINING THESE COMPOUNDS

The present invention relates to novel N-substituted 2-methylnaphthylamides, processes for their preparation, and fungicides which contain these compounds.

The use of zinc ethylene-1,2-bis-dithiocarbamate, of N-trichloromethylthiophthalimide and of N-trichloromethylthiotetrahydrophthalimide as fungicides in agriculture and horticulture has been disclosed. The said compounds are effective agents for combating fungal diseases (cf. R. Wegler, "Chemie der Pflanzenschutz- und Schädlingsbekämpfungsmittel", volume 2, pages 65–66 and 109, and volume 4, pages 139 and 191, Springer Verlag Berlin/Heidelberg/New York (1970) and (1977)).

However, these fungicides cannot be used after infection has occurred, and their effect when used at low concentrations does not satisfy actual requirements.

We have found that novel N-substituted 2-methylnaphthylamides of the general formula I

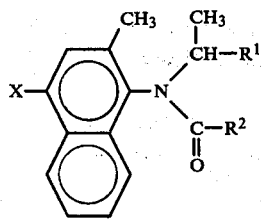

where $R^1$ is

$R^3$ being hydrogen or $C_1$–$C_4$-alkoxy, or $R^1$ is

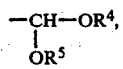

$R^4$ and $R^5$ independently of one another being unsubstituted or substituted $C_1$–$C_4$-alkyl or $R^4$ and $R^5$ together being an alkylene group which, together with the radical on which they are present as substituents, forms a 5-membered or 6-membered heterocyclic ring which contains two oxygen atoms and is unsubstituted or substituted by $C_1$–$C_4$-alkyl or aryl, and $R^2$ is $C_1$–$C_4$-alkyl which is unsubstituted or substituted by fluorine, chlorine, bromine, iodine, $C_1$–$C_4$-alkoxy, $C_1$–$C_4$-alkylthio, imidazol-1-yl, pyrazol-1-yl, 1,2,4-triazol-1-yl or oxo (=O), or is $C_2$–$C_5$-alkenyl, $C_2$–$C_5$-alkynyl, $C_3$–$C_7$-cycloalkyl, $C_4$–$C_7$-cycloalkenyl, $C_1$–$C_5$-alkoxy, unsubstituted or substituted phenyl or unsubstituted or substituted hetaryl, and X is hydrogen, methyl, chlorine or bromine, exhibit powerful fungicidal properties.

In formula I, $R^2$ is preferably linear or branched $C_1$–$C_5$-alkoxy, eg. methoxy, ethoxy, n-propoxy, iso-propoxy, n-butoxy, iso-butoxy, sec.-butoxy, tert.-butoxy, n-pentoxy or iso-pentoxy, or is branched or linear $C_1$–$C_4$-alkyl, eg. methyl, ethyl, n-propyl, iso-propyl, n-butyl, iso-butyl, sec.-butyl or tert.-butyl, which is unsubstituted or substituted by fluorine, chlorine, bromine, iodine, methoxy, ethoxy, butoxy, methylthio, ethylthio, imidazol-1-yl, pyrazol-1-yl or 1,2,4-triazol-1-yl.

Further examples of $R^2$ are vinyl, prop-1-enyl, prop-2-enyl, allyl or ethynyl; cycloalkyl or cycloalkenyl of 3 to 7 ring carbon atoms, eg. cyclopropyl, cyclopentyl, cyclohexyl or cyclohex-2-enyl; unsubstituted or substituted phenyl; and unsubstituted or substituted hetaryl with 5 or 6 ring atoms, of which 1–3, in particular 1 or 2, are hetero-atoms and may be identical or different and are preferably oxygen, nitrogen or sulfur, eg. a furan, thiophene, isoxazole or pyridine radical.

Examples of preferred substituents of the above aromatic and heteroaromatic radicals $R^2$ are: halogen, especially fluorine, chlorine or bromine; nitro; linear alkyl of 1 to 4 carbon atoms; alkoxy or alkylthio of 1 to 4 carbon atoms, eg. methoxy, ethoxy, methylthio, ethylthio or n-propylthio; haloalkyl, haloalkoxy or haloalkylthio of up to 4 carbon atoms and up to 8 halogen atoms (especially fluorine and chlorine), eg. trichloromethyl, trifluoromethyl and tetrafluoroethoxy; cyano, alkylcarbonyl or alkoxycarbonyl, eg. methoxycarbonyl, acetyl and propionyl; and unsubstituted or substituted phenyl and phenylcarbonyl.

$R^3$ is in particular hydrogen or branched or linear $C_1$–$C_4$-alkoxy, eg. methoxy, ethoxy, n-propoxy, iso-propoxy, n-butoxy, iso-butoxy, sec.-butoxy and tert.-butoxy.

Examples of $R^4$ and $R^5$ are unsubstituted or substituted linear or branched alkyl of up to 4 carbon atoms, eg. methyl, ethyl, n-propyl, iso-propyl, n-butyl and iso-butyl. Further, $R^4$ and $R^5$ together may be, alkylene of 2 or 3 carbon atoms which is unsubstituted or substituted by alkyl of up to 4 carbon atoms, e.g. methyl or ethyl.

X is preferably hydrogen, methyl, chlorine or bromine.

The novel N-substituted 2-methylnaphthylamides of the formula I have a chiral carbon atom with H, $CH_3$, $R^1$ and

as ligands and with further chirality centers, depending on the nature of $R^2$, $R^3$, $R^4$ and $R^5$. The optically pure enantiomers and the diastereomers can be obtained by conventional methods. The present invention also encompasses these compounds in the pure form or in the form of mixtures. The pure enantiomers, the individual diastereomers and the mixtures usually obtained from the process of synthesis are all active as fungicides.

Further, we have found that the novel compounds of the general formula (I) are obtained when a 2-methylnaphthylamine of the formula II

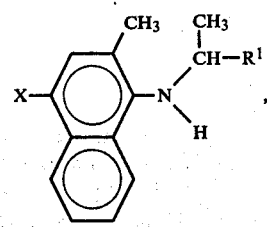

where $R^1$ and X have the above meanings, is reacted (a) with an acid halide of the formula III

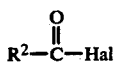

or (b) with an acid anhydride of the formula IV

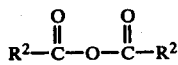

where $R^2$ has the above meanings and Hal is chlorine or bromine, in the presence or absence of a solvent or diluent, with or without addition of an inorganic or organic base and with or without addition of a reaction accelerator, at from $-10°$ to $100°$ C. Reactions (a) and (b) are preferred. Examples of preferred solvents or diluents which are inert to the reactants are aliphatic and aromatic hydrocarbons, e.g. pentane, cyclohexane, petroleum ether, benzene, toluene and xylenes; halohydrocarbons, eg. methylene chloride, chloroform, 1,2-dichloroethane and chlorobenzene; ketones, eg. acetone and methyl ethyl ketone; ethers, eg. diethyl ether, dimethoxyethane, tetrahydrofuran and dioxane; esters, eg. ethyl acetate; nitriles, eg. acetonitrile; sulfoxides, eg. dimethylsulfoxide; and mixtures of these.

Examples of suitable inorganic and organic bases which may also be used as acid acceptors in the reaction are alkali metal carbonates and alkaline earth metal carbonates, eg. sodium bicarbonate, potassium bicarbonate, sodium carbonate, potassium carbonate and calcium carbonate; borates, eg. sodium borate; phosphates, eg. sodium diphosphate and triphosphate and potassium diphosphate and triphosphate; and amines, eg. triethylamine, N,N-dimethylaniline, N,N-dimethylcyclohexylamine, N-methylpiperidine and pyridine. However, other conventional bases may also be used.

Preferred reaction accelerators are metal halides, eg. sodium bromide and potassium iodide, azoles, eg. imidazole and 1,2,4-triazole, and pyridines, eg. 4-dimethylaminopyridine.

The reactions according to the invention are carried out at, for example, from $-10°$ to $+100°$ C., preferably from $0°$ to $+40°$ C., under atmospheric or superatmospheric pressure, continuously or batchwise.

Further, we have found that compounds of the formula I are obtained when a 2-methylnaphthylamide of the formula Ia

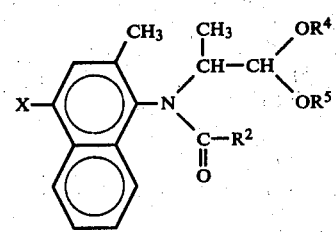

where $R^2$ and X have the above meanings and $R^4$ and $R^5$ independently of one another are unsubstituted or substituted $C_1$-$C_4$-alkyl, is converted to the corresponding aldehyde by splitting off $R^4$ and $R^5$, or is converted to the corresponding cyclic acetal by reaction with a diol HO—$R^4$—$R^5$—OH, where $R^4$ and $R^5$ together are alkylene, in the presence or absence of a diluent and in the presence or absence of an acid catalyst.

Examples of the above diols include ethylene glycol, 1,2-propylene glycol, propane-1,3-diol, butane-2,3-diol and neopentylglycol. The splitting off of $R^4$ and $R^5$ is effected, for example, by treatment with catalytic amounts of strong protic acids or Lewis acids, eg. hydrogen chloride (or hydrochloric acid), hydrogen bromide, p-toluenesulfonic acid, trifluoroacetic acid, trifluoromethylsulfonic acid, zinc chloride, zinc bromide or boron trifluoride etherate, at from $0°$ C. to the boiling point of the alcohols $R^4$—OH and $R^5$—OH which are split off. The reaction with a 1,2- or 1,3-diol is effected, for example, by removing the alcohols $R^4$—OH and $R^5$—OH from the reaction mixture by distillation under reduced pressure or under atmospheric pressure, or by sweeping out with an inert gas, e.g. nitrogen or argon. Suitable solvents and diluents are those stated to be preferred for reaction IV above, or water, or the 1,2- or 1,3-diols themselves if the stoichiometric amount or an excess is used.

Suitable acid catalysts are Lewis acids or proton acids, eg. $BF_3$, $AlCl_3$, $ZnCl_2$, mineral acids and sulfonic acids.

Further, compounds of the general formula I are obtained when a 2-methylnaphthylamide of the formula Ib

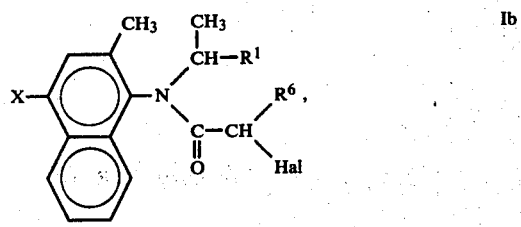

where $R^1$ and X have the above meanings, Hal is halogen and $R^6$ is hydrogen, $C_1$-$C_3$-alkyl, $C_2$-$C_4$-alkenyl, $C_3$-$C_7$-cycloalkyl or $C_1$-$C_5$-alkoxy, is reacted with a nucleophilic compound of the formula V

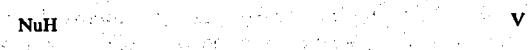

where Nu is $C_1$-$C_5$-alkoxy, $C_1$-$C_4$-alkylthio, imidazol-1-yl, pyrazol-1-yl or 1,2,4-triazol-1-yl, in the presence or absence of a solvent or diluent, in the presence or absence of an inorganic or organic base, and in the presence or absence of a reaction accelerator, at from $-10°$ to $+100°$ C.

Further compounds of the general formula I are obtained when conventional secondary chemical reactions are carried out, depending on the functional nature of $R^1$ and $R^2$.

The 2-methylnaphthylamines of the formula II used as starting materials for the preparation of the compounds of the formula I are obtained when a 2-methylnaphthylamine of the formula VI

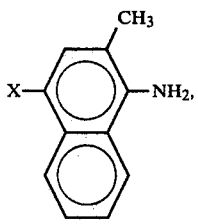

where X has the above meanings, is reacted (a) with a 2-halopropionic acid ester of the formula VII

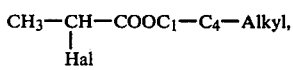

where Hal is chlorine or bromine, or (b) with 2-halopropanol dialkylacetal of the formula VIII

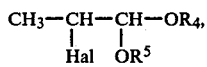

where Hal is chlorine or bromine, and $R^4$ and $R^5$ have the above meanings, in the presence or absence of a solvent or diluent, in the presence or absence of an inorganic or organic base and in the presence or absence of a reaction accelerator, at from $-10°$ to $+130°$ C.

The preferred solvents and diluents, the inorganic or organic bases and the reaction accelerators include the compounds mentioned above.

Further, we have found that the compounds of the general formula II are obtained when (a) a 2-methylnaphthylamine of the formula IIb is reacted with a pyruvic acid ester of the formula IX

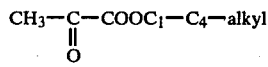

or with a methylglyoxal acetal of the formula XI

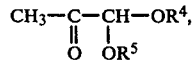

where $R^4$ and $R^5$ have the above meanings, and (b) the Schiff base obtained as the reaction product is hydrogenated, for example with a complex metal hydride or catalytically with hydrogen.

The Schiff base is prepared, for example, by reacting 1 mole of the 2-methylnaphthylamine of the formula VI with from 0.9 to 1.5 moles of the pyruvic acid ester of the formula IX or of the methylglyoxal acetal of the formula XI, in a solvent, with or without addition of an acid catalyst, and removing water by distillation at from 40° to 200° C., preferably from 50° to 120° C. Advantageously, solvents which are inert under the reaction conditions and form azeotropes with water are used for the reaction. Examples of suitable solvents include aromatic hydrocarbons, eg. benzene, toluene, ethylbenzene, o-, m- and p-xylene, isopropylbenzene and methylnaphthalene; aliphatic and cycloaliphatic hydrocarbons, eg. heptane, nonane, pinane, gasoline fractions having a boiling range of from 70° to 190° C., cyclohexane, methylcyclohexane, decalin, naphtha, 2,2,4-trimethylpentane, 2,2,3-trimethylpentane, 2,3,3-trimethylpentane and octane; and mixtures of the above.

The hydrogenation may be carried out either by reduction with a complex hydride, such as NaBH$_4$, or by catalytic hydrogenation with hydrogen.

The reduction with sodium borohydride is in general carried out by reacting 1 mole of Schiff base with from 0.2 to 1 mole of sodium borohydride in a solvent at from $-20°$ to $+40°$ C.

In carrying out the catalytic hydrogenation, hydrogen is fed to the reaction mixture at the start of, and during, the reaction in such amount that the reaction pressure at the reaction temperature is always an appropriate one, advantageously from 150 to 300 bar. The reaction is in general carried out at from 20° to 200° C., preferably from 25° to 160° C., batchwise or continuously. Inert gases, eg. nitrogen, may also be used to set up the appropriate pressure.

Particularly suitable solvents or diluents for both embodiments of the hydrogenation are alkanols and cycloalkanols, eg. n-propanol, isopropanol, n-butanol, isobutanol, glycol, ethylene glycol monoethyl ether, glycerol, amyl alcohol, cyclohexanol, 2-methyl-pentan-4-ol, 2-ethylhexanol and especially methanol and ethanol, and cyclic ethers, eg. tetrahydrofuran and dioxane.

For the catalytic hydrogenation, the amount of catalyst used is as a rule from 5 to 30 percent by weight of the weight of Schiff base. The catalyst may be used as a mixture with a carrier appropriate for the reaction, for example silicon dioxide, the amount of catalyst advantageously being from 10 to 40 percent by weight of the mixture of catalyst and carrier.

Advantageous catalysts to use are copper chromite catalysts, eg. copper/chromium oxide catalysts, such as the copper chromites used by H. Adkins (cf. Houben-Weyl, Methoden der organischen Chemie, volume 4/2, pages 180–183, and J. Appl. Chem. 5 (1955), 289–295). These contain, for example, a copper-chromium spinel (CuCr$_2$O$_4$) or a mixture in the ratio of 5 CuO:4 Cr$_2$O$_3$, or are based on such compounds or mixtures, and may additionally contain other oxides, in the main the oxides of alkaline earth metals, eg. of magnesium, calcium or barium.

The process descriptions which follow illustrate the preparation of 2-methylnaphthylamines of the formula II:

(a) direct alkylation of 1-amino-2-methylnaphthalene

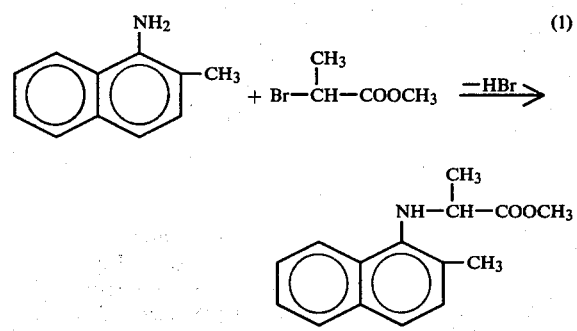

144.2 g of 1-amino-2-methylnaphthalene (0.92 mole), 90.2 g (1.08 moles) of sodium bicarbonate and 460 g (2.76 moles) of methyl 2-bromopropionate are stirred for 18 hours at 120°–125° C. When the mixture has cooled, the precipitate is filtered off and the filtrate is concentrated under reduced pressure. The residue is distilled under reduced pressure. 188 g (83.7% of theory) of methyl N-(2-methyl-naphth-1-yl)-alanate are obtained as a colorless oil. Boiling point: 138°–140° C./0.2 mbar.

(b) Schiff base of 1-amino-2-methylnaphthalene

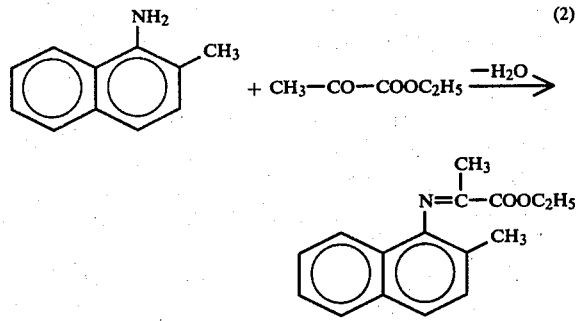

314 g of 1-amino-2-methylnaphthalene (2 moles), 232 g of ethyl pyruvate (2 moles) and 0.4 g of p-toluenesulfonic acid in 1,000 ml of cyclohexane are refluxed for 4 hours, at which stage 36 g of water have distilled off azeotropically and been separated from the distillate. The cyclohexane is then distilled off under reduced pressure and the residue is directly reacted further.

Yield: 494.7 g (97% of theory) of Schiff base.

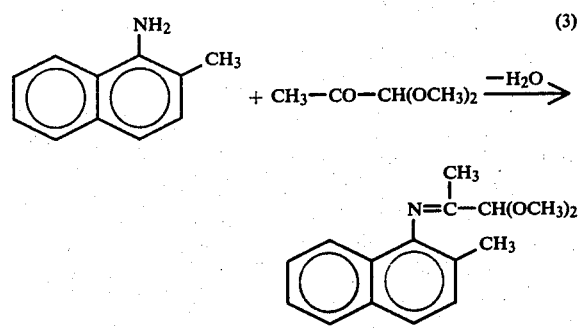

314 g of 1-amino-2-methylnaphthalene, 236 g of methylglyoxal dimethylacetal and 0.4 g of p-toluene-sulfonic acid are reacted similarly to process (b), equation (2).

Yield: 493.4 g of Schiff base
(c) Hydrogenation of the Schiff base

Catalytic hydrogenation

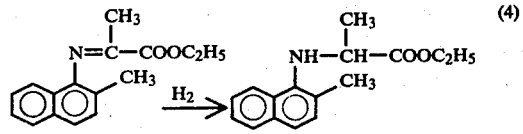

A hydrogenation autoclave having a volume of 1 liter is charged with 200 g of the Schiff base of 1-amino-2-methylnaphthalene and methyl pyruvate, dissolved in 500 parts of tetrahydrofuran, and 15 parts of Adkins catalyst (copper chromite powder). The autoclave is then heated to 150° C. and hydrogen is forced in until the pressure reaches 200 bar. As soon as the absorption of hydrogen has ceased and a constant pressure is reached (after about 9 hours), the mixture is cooled, the catalyst is filtered off and the filtrate is distilled under reduced pressure.

142 g (71% of theory) of ethyl N-(2-methyl-naphth-1-yl)-alanate are obtained as a colorless oil of boiling point 144°–145° C./0.15 mbar. Reduction with NaBH$_4$ 490 g of the Schiff base of 1-amino-2-methylnaphthalene and methylglyoxal dimethylacetal are dissolved in 1,500 ml of methanol and 60 g of sodium borohydride are added in portions at 0° C. After the mixture has been stirred overnight, the methanol is distilled off, the residue is dissolved in 1,000 ml of methylene chloride, this solution is stirred for 30 minutes with 500 ml of 10% strength potassium hydroxide solution, and the organic phase is separated off. It is washed three times with 200 ml of water at a time, and dried over sodium sulfate, the methylene chloride is distilled off and the residue is distilled under reduced pressure.

367 g (74% of theory) of 2-(N-2'-methyl-naphth-1'-yl)-aminopropanal dimethylacetal of boiling point 140°–145° C./0.3 mbar are obtained.

The following compounds may also be prepared by the general methods described above:

Methyl 2-N-[(pyrazol-1-yl)-acetyl]-N-(2'-methyl-naphth-1'-yl)-alanate, ethyl 2-N-[(pyrazol-1-yl)-acetyl]-N-(2'-methyl-naphth-1'-yl)-alanate, methyl 2-N-[(1,2,4-triazol-1-yl)-acetyl]-N-(2'-methyl-naphth-1'-yl)-alanate, ethyl 2-N-[(1,2,4-triazol-1-yl)-acetyl]-N-(2'-methyl-naphth-1'-yl)-alanate, methyl 2-N-cyclopropyl-carbonyl-N-(2-methyl-naphth-1-yl)-alanate, ethyl 2-N-cyclopropylcarbonyl-N-(2-methyl-naphth-1-yl)-alanate, methyl 2-N-cyclopentylcarbonyl-N-(2-methyl-naphth-1-yl)-alanate, methyl 2-N-cyclohexylcarbonyl-N-(2-methyl-naphth-1-yl)-alanate, methyl 2-N-methoxycarbonyl-N-(2-methyl-naphth-1-yl)-alanate, methyl 2-N-ethoxycarbonyl-N-(2-methyl-naphth-1-yl)-alanate, ethyl 2-N-ethoxycarbonyl-N-(2-methyl-naphth-1-yl)-alanate, methyl 2-N-propoxycarbonyl-N-(2-methyl-naphth-1-yl)-alanate, methyl 2-N-allyloxycarbonyl-N-(2-methoxy-naphth-1-yl)-alanate, methyl 2-N-butoxycarbonyl-N-(2-methoxy-naphth-1-yl)-alanate, methyl 2-N-methoxalyl-N-(2-methoxy-naphth-1-yl)-alanate, methyl 2-N-ethoxalyl-N-(2-methoxy-naphth-1-yl)-alanate, ethyl 2-N-ethoxalyl-N-(2-methyl-naphth-1-yl)-alanate, methyl 2-N-acetoacetyl-N-(2-methyl-naphth-1-yl)-alanate, methyl 2-N-(4-oxo-pentanoyl)-N-(2'-methyl-naphth-1'-yl)-alanate, methyl 2-N-(3-hydroxybutyryl)-N-(2'-methyl-naphth-1'-yl)-alanate, methyl 2-N-benzoyl-N-(2-methyl-naphth-1-yl)-alanate, methyl 2-N-(2-chlorobenzoyl)-N-(2'-methyl-naphth-1'-yl)-alanate, methyl 2-N-(2-bromobenzoyl)-N-(2'-methyl-naphth-1'-yl)-alanate, methyl 2-N-(2-iodobenzoyl)-N-(2'-methyl-naphth-1'-yl)-alanate, methyl 2-N-(2-methylbenzoyl)-N-(2'-methyl-naphth-1'-yl)-alanate, methyl 2-N-(2-trifluoromethylbenzoyl)-N-(2'-methyl-naphth-1'-yl)-alanate, methyl 2-N-(2-methoxybenzoyl)-N-(2'-methyl-naphth-1'-yl)-alanate, methyl 2-N-(thiophene-2-carbonyl)-N-(2'-methyl-naphth-1'-yl)-alanate, methyl 2-N-(furan-2-carbonyl)-N-(2'-methyl-naphth-1'-yl)-alanate, ethyl 2-N-(furan-2-carbonyl)-N-(2'-methyl-naphth-1'-yl)-alanate, methyl 2-N-(2-methylfuran-3-carbonyl)-N-(2'-methyl-naphth-1'-yl)-alanate, methyl 2-N-(2,5-dimethylfuran-3-carbonyl)-N-(2'-methyl-1'-methyl-naphth-1'-yl)-alanate, methyl 2-N-(2,4,5-trimethylfuran-3-carbonyl)-N-(2'-methyl-naphth-1'-yl)-alanate, methyl 2-N-(isoxazolyl-3-carbonyl)-N-(2'-methyl-naphth-1'-yl)-alanate, ethyl 2-N-(isoxazolyl-3-carbonyl)-N-(2'-methyl-naphth-1'-yl)-alanate, methyl 2-N-(3- methylisoxazolyl-5-carbonyl)-N-(2'-methyl-naphth-1'-yl)-alanate, methyl 2-N-nicotinoyl-N-(2-methyl-naphth-1-yl)-alanate, methyl 2-N-(2-chloronicotinoyl)-N-(2'-methyl-naphth-1'-yl)-alanate, methyl 2-N-acryloyl-N-(2-methyl-naphth-1-yl)-alanate, methyl 2-N-(2-methylacryloyl)-N-(2-methyl-naphth-1-yl)-alanate, methyl 2-N-phenoxycarbonyl-N-(2-methyl-naphth-1-yl)-alanate, methyl 2-N-(4-chlorophenoxycarbonyl)-N-(2'-methyl-naphth-1'-yl)-alanate, 2-[N-(2-methyl-naphth-1-yl)-N-acetyl]-aminopropanol dimethylacetal, 2-[N-(2-methyl-naphth-1-yl)-N-propionyl]-aminopropanal dimethylacetal, 2-[N-(2-methyl-naphth-1-yl)-N-butyryl]-aminopropanal dimethylacetal, 2-[N-(2-methyl-naphth-1-yl)-N-chloroacetyl]-aminopropanal dimethylacetal, chloroacetic acid N-[1-(1,3-dioxolan-2-yl)-ethyl]-N-2'-methyl-naphthyl-1''-amide, chloroacetic acid N-[1-(4'-methyl-1',3'-dioxolan-2'-yl)-ethyl]-N-2''-methyl-naphthyl-1''-amide, 2-[N-(2-methyl-naphth-1-yl)-N-bromoacetyl]-aminopropanal dimethylacetal, 2-[N-(2-methyl-naphth-1-yl)-N-iodoacetyl]-aminopropanal dimethylacetal, 2-[N-(2-methyl-naphth-1-yl)-N-methoxyacetyl]-aminopropanal dimethylacetal, methoxyacetic acid N-[1,3-dioxolan-2-yl)-ethyl]-N-2'-methyl-naphthyl-1'-amide, methoxyacetic acid N-[1-(4'-methyl-1',3'-dioxolan-2'-yl)-ethyl]-N-2''-methyl-naphthyl-1''-amide, methoxyacetic acid N-[1-(4',5'-dimethyl-1',3'-dioxolan-2'-yl)-ethyl]-N-2''-methyl-naphthyl-1''-amide, 2-[N-(2-methyl-naphth-1-yl)-N-ethoxyacetyl]-aminopropanal dimethylacetal, 2-[N-(2-methyl-naphth-1-yl)-N-methylthioacetyl]-aminopropanal dimethylacetal, 2-[N-(2-methyl-naphth-1-yl)-N-(2'-chloropropionyl)]-aminopropanal dimethylacetal, 2-[N-(2-methyl-naphth-1-yl)-N-(imidazol-1'-ylacetyl)]-aminopropanal dimethylacetal, 2-[N-(2-methyl-naphth-1-yl)-N-(pyrazol-1'-ylacetyl)]-aminopropanal dimethylacetal, 2-[N-(2-methyl-naphth-1-yl)-N-(1',2',4'-triazol-1'-ylacetyl)]-aminopropanal dimethylacetal, 2-[N-(2-methyl-naphth-1-yl)-N-cyclopropylcarbonyl]-aminopropanal dimethylacetal, 2-[N-(2-methyl-naphth-1-yl)-N-cyclohexylcarbonyl]-aminopropanal dimethylacetal, 2-[N-(2-methyl-naphth-1-yl)-N-methoxycarbonyl]-aminopropanal dimethylacetal, 2-[N-(2-methyl-naphth-1-yl)-N-ethoxycarbonyl]-aminopropanal dimethylacetal, 2-[N-(2-methyl-naphth-1-yl)-N-butoxycarbonyl]-aminopropanal dimethylacetal, 2-[N-(2-methyl-naphth-1-yl)-N-allyloxycarbonyl]-aminopropanal dimethylacetal, 2-[N-(2-methyl-naphth-1-yl)-N-methoxalyl]-aminopropanal dimethylacetal, 2-[N-(2-methyl-naphth-1-yl)-N-ethoxalyl]-aminopropanal dimethylacetal, 2-[N-(2-methyl-naphth-1-yl)-N-acetoacetyl]-aminopropanal dimethylacetal, acetoacetic acid N-[1-(1,3-dioxolan-2-yl)-ethyl]-N-2'-methyl-naphthyl-1'-amide, 2-[N-(2-methyl-naphth-1-yl)-N-(3'-hydroxy-butyryl)]-aminopropanal dimethylacetal, 2-[N-(2-methyl-naphth-1-yl)-N-benzoyl]-aminopropanal dimethylacetal, 2-[N-(2-methyl-naphth-1-yl)-N-(2'-chlorobenzoyl)]-aminopropanal dimethylacetal, 2-[N-(2-methyl-naphth-1-yl)-N-(2'-bromobenzoyl)]-aminopropanal dimethylacetal, 2-[N-(2-methyl-naphth-1-yl)-N-(2'-trifluoromethylbenzoyl)]-aminopropanal dimethylacetal, 2-[N-(2-methyl-naphth-1-yl)-N-(2'-methoxybenzoyl)]-aminopropanal dimethylacetal, 2-[N-(2-methyl-naphth-1-yl)-N-(furan-2-carbonyl)]-aminopropanal dimethylacetal, furan-2-carboxylic acid N-[1,3-dioxolan-2-yl)-ethyl]-N-2'-methyl-naphthyl-1'-amide, 2-[N-(2-methyl-naphth-1-yl)-N-(2'-methylfuran-3'-carbonyl)]-aminopropanal dimethyl-acetal, 2-[N-(2-methyl-naphth-1-yl)-N-(2',4',5'-trimethyl-furan-3'-carbonyl)]-aminopropanal dimethylacetal, 2-[N-(2-methyl-naphth-1-yl)-N-(isoxazolyl-3'-carbonyl)]-aminopropanal dimethylacetal, 2-[N-methyl-naphth-1-yl)-N-(3'-methyl-isoxazol-5'-yl-carbonyl)]-aminopropanal dimethylacetal, 2-[N-(2-methyl-naphth-1-yl)-N-nicotinoyl]-aminopropanal dimethylacetal, 2-[N-(2-methyl-naphth-1-yl)-N-(2'-chloronicotinoyl)]-aminopropanal dimethylacetal, 2-[N-(2-methyl-naphth-1-yl)-N-acryloyl]-aminopropanal dimethylacetal, 2-[N-(2-methyl-naphth-1-yl)-N-(4'-chlorophenoxycarbonyl)]-aminopropanal dimethylacetal, methyl N-(furan-2-carbonyl)-N-(2'-methyl-4'-bromo-naphth-1'-yl)-alanate, methyl N-methoxyacetyl-N-(2-methyl-4-bromo-naphth-1-yl)-alanate, 2-[N-(2-methyl-naphth-1-yl)-N-bromoacetyl]-aminopropionaldehyde and 2-[N-(2-methyl-naphth-1-yl)-N-methoxyacetyl]-aminopropionaldehyde.

The Examples which follow illustrate the preparation of the novel compounds.

EXAMPLE 1

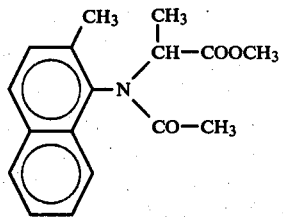

A mixture of 30.7 g (0.12 mole) of methyl N-(2-methyl-naphth-1-yl)-alanate, 9.5 g of pyridine (0.12 mole), 5 g of 4-dimethylaminopyridine and 50 ml of acetic anhydride is stirred for 8 hours at 80° C. and is then cooled and concentrated under reduced pressure. 250 ml of diethyl ether and 250 ml of water are added to the residue. The organic phase is separated off, washed with 100 ml of 1 N hydrochloric acid and then with 100 ml of water, decolorized with charcoal and concentrated. The residue is stirred with 30 ml of a 5:1 petroleum ether/ether mixture at 0° C. and left to crystallize for 4 hours at 0° C., and the crystals are filtered off. 23.6 g (69% of theory) of methyl N-acetyl-N-(2-methyl-naphth-1-yl)-alanate are obtained as white crystals of melting point 119°–121° C.

EXAMPLE 2

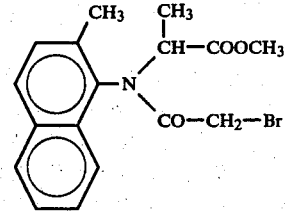

19.4 g (0.09 mole) of methyl N-(2-methyl-naphth-1-yl)-alanate are added to a well-stirred suspension of 14 g of sodium bicarbonate (0.17 mole) and 20 g of sodium sulfate in 150 ml of dry toluene, and a solution of 24.2 g (0.12 mole) of bromoacetyl bromide and 50 ml of toluene is then added dropwise in the course of 1 hour at +15° C. After the mixture has been stirred for 5 hours at 25° C., the precipitate is filtered off and washed with 50 ml of toluene. The filtrate is washed twice with 100 ml of 1 N sodium hydroxide solution at a time, once with 50 ml of 2 N hydrochloric acid and finally with 100 ml of water, dried, decolorized with charcoal and concentrated under reduced pressure. The oily residue is dried for 3 hours at 50° C. and 0.1 mbar. 22.5 g (77.3% of theory) of methyl N-bromoacetyl-N-(2-methyl-naphth-1-yl)-alanate are obtained as a pale yellow oil.

IR spectrum (film): 3035, 2970, 2935, 1730, 1652, 1440, 1415, 1360, 1200, 1132, 1095, 812, 782 and 744 cm$^{-1}$.

EXAMPLE 3

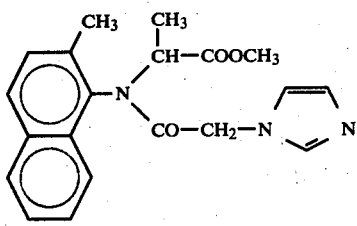

13 g (0.036 mole) of methyl N-bromoacetyl-N-(2-methyl-naphth-1-yl)-alanate (Example 2) are dissolved in 60 ml of dry dimethylformamide and 6.8 g (0.1 mole) of imidazole are added. The mixture is stirred for 10 hours at 60° C. and concentrated under reduced pressure. The residue is extracted by shaking with 150 ml of methylene chloride and 50 ml of water and the organic layer is separated off and washed twice with 50 ml of water at a time. Thereafter the organic solution is dried, decolorized with charcoal and concentrated. The crude product is purified by filtering its solution in ethyl acetate over silica gel; on evaporating off the ethyl acetate, a residue of 9.6 g of resin is obtained.

calculated: C 68.4 H 6.0 N 12.0%; found: C 68.0 H 6.4 N 11.9%.

EXAMPLE 4

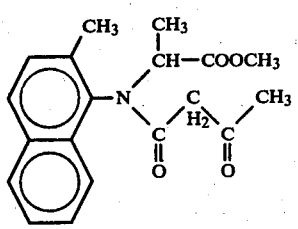

9 g (0.1 mole) of diketene are added dropwise to 24.3 g (0.1 mole) of methyl N-(2-methyl-naphth-1-yl)-alanate and 0.5 ml of triethylamine in 50 ml of dry toluene at 80°–90° C., whilst stirring. After the mixture has been stirred for 3 hours at 95° C., it is cooled, washed once with 50 ml of 2 N hydrochloric acid and once with water, dried and concentrated. The crude product is purified by filtering its solution in ethyl acetate over silica gel; on evaporating off the ethyl acetate, a residue of 29.7 g of analytically pure oil is obtained (yield 90% of theory).

IR spectrum (film): 3042, 2980, 2940, 1740, 1720, 1650, 1455, 1370, 1310, 1195, 920, 815, 786 and 746 cm$^{-1}$.

EXAMPLE 5

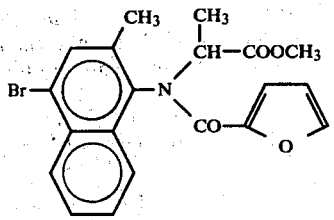

11 g (0.067 mole) of bromine are added to 22.2 g (0.066 mole) of methyl N-(furan-2-carbonyl)-N-(2-methyl-naphth-1-yl)-alanate (Example 21) and 6 g (0.07 mole) of anhydrous sodium acetate in 150 ml of acetic acid, and the mixture is stirred for 24 hours at 35° C. It is then stirred into 700 ml of ice water and the product is extracted three times with 100 ml of ether at a time. The combined ether extracts are washed once with 100 ml of 1 N sodium hydroxide solution and once with water, dried and concentrated.

17 g (62% of theory) of methyl N-(furan-2-carbonyl)-N-(2'-methyl-4'-bromo-naphth-1'-yl)-alanate are obtained as a colorless resin.

IR spectrum (film): 3035, 2930, 1730, 1640, 1450, 1360, 1235, 1190, 1126, 1092, 908 and 810 cm$^{-1}$.

EXAMPLE 6

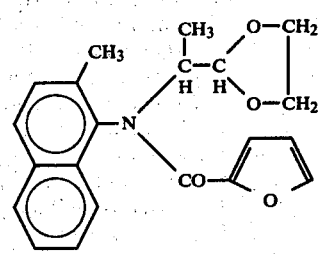

14.2 g (0.04 mole) of 2-[N-(2-methyl-naphth-1-yl)-N-(furan-2-carbonyl)]-aminopropanal dimethylacetal (Example No. 23), 3 ml of ethylene glycol and 0.2 g of p-toluenesulfonic acid in 80 ml of toluene are stirred for 8 hours at 80° C., whilst constantly stripping the resulting methanol from the reaction mixture by means of a gentle stream of nitrogen. After cooling the mixture and washing it three times with 60 ml of water at a time, the organic solution is decolorized with charcoal and concentrated under reduced pressure. The residue crystallizes after addition of 10 ml of cold ether. 9 g (64% of theory) of furan-2-carboxylic acid N-[1-(1,3-dioxolan-2-yl)-2-methyl-ethyl]-N-2'-methyl-naphthyl-1'-amide are obtained as white crystals of melting point 129°–131° C.

EXAMPLE 7

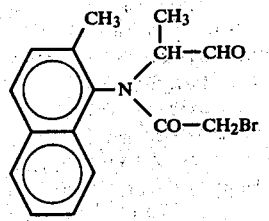

7.6 g (0.02 mole) of 2-[N-(2-methyl-naphth-1-yl)-N-bromoacetyl]-aminopropanal dimethylacetal (Example No. 13), dissolved in 50 ml of methylene chloride, are stirred vigorously with 100 ml of 2 N hydrochloric acid for 1 hour at room temperature. The organic phase is separated off, washed with 100 ml of water, dried and concentrated. 5.3 g (80% of theory) of 2-[N-(2-methyl-naphth-1-yl)-N-bromoacetyl]-aminopropionaldehyde are obtained as a pale yellow oil.

IR (film): 3038, 2970, 2820, 2710, 1720, 1645, 1490, 1365, 1203, 810, 778, 742 and 640 cm$^{-1}$.

The following compounds are prepared similarly:

TABLE 1

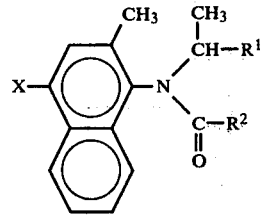

| Ex. no. | X | R$^1$ | R$^2$ | M.p. °C. | IR(film) [cm$^{-1}$] |
|---|---|---|---|---|---|
| 8 | H | —CH(OCH$_3$)$_2$ | —CH$_3$ | oil | 3042, 2980, 2930, 1645, 1448, 1360, 1295, 1148, 1120, 1062, 945, 814, 786, 747. |
| 9 | H | —CH(OCH$_3$)$_2$ | —C$_2$H$_5$ | oil | 2972, 2928, 1642, 1445, 1365, 1256, 1120, 1080, 1060, 952, 811, 783, 744. |
| 10 | H | —COOCH$_3$ | —CH$_2$—Cl | oil | 3042, 2980, 2940, 1740, 1622, 1505, 1365, 1240, 1200, 1105, 1050, 815, 783, 748. |
| 11 | H | —CH(OCH$_3$)$_2$ | —CH$_2$Cl | 80–82 | |
| 12 | H | —COOCH$_3$ | —O—CH$_3$ | resin | 3040, 2940, 2910, 1732, 1690, 1430, 1325, 1190, 1066, 1025, 810, 785, 772, 742. |
| 13 | H | —CH(OCH$_3$)$_2$ | —CH$_2$Br | resin | 3018, 2912, 2810 1645, 1585, 1556, 1415, 1256, 1235, 1138, 1085, 810, 780. |
| 14 | H | —COOCH$_3$ | —C$_2$H$_5$ | oil | 3045, 2972, 1720, 1648, 1440, 1390, 1260, 1170, 1130, 1075, 812, 780, 644. |
| 16 | H | —COOCH$_3$ | —CH$_2$—O—CH$_3$ | oil | 3042, 2935, 1732, 1664, 1440, 1380, 1280, 1190, 1125, 812, 784, 746. |
| 18 | H | (dioxolane) | —CH$_2$—O—CH$_3$ | 107–109 | |
| 19 | H | —COOCH$_3$ | —CH$_2$—S—CH$_3$ | oil | 3035, 2975, 2935, 1730, 1640, 1440, 1359, 1210, 1185, 1100, 1043, 978, 810, 780, 744. |
| 20 | H | —COOCH$_3$ | —CH$_2$—N(triazolyl) | 106–108 | |
| 21 | H | —COOCH$_3$ | (furyl) | oil | 3040, 2980, 2938, 1712, 1630, 1548, 146, 1400, 1304, 1246, 1190, 1098, 1010, 814, 780, 762. |

TABLE 1-continued

[Structure: naphthalene with X substituent, CH₃ group, N attached with CH(CH₃)–R¹ and C(=O)–R²]

| Ex. no. | X | R¹ | R² | M.p. °C. | IR(film) [cm⁻¹] |
|---|---|---|---|---|---|
| 22 | H | —COOC₂H₅ | [furan-2-yl] | oil | 3130, 2982, 2935, 2900, 1710, 1630, 1550, 1450, 1402, 1302, 1240, 1095, 1070, 812, 7... 760. |
| 23 | H | —CH(OCH₃)₂ | [furan-2-yl] | oil | 2968, 2925, 1625, 1555, 1455, 1376, 1305, 1174, 1100, 1058, 810, 795, 779, 750. |
| 24 | H | —COOCH₃ | [isoxazol-3-yl] | resin | 3108, 3038, 2935, 1726, 1635, 1532, 14.., 1330, 1200, 1100, 1042, 875, 856, 810, 796, 778, 758, 742. |
| 25 | H | —CH(OCH₃)₂ | [isoxazol-3-yl] | resin | 3105, 3040, 2930, 1640, 1544, 1438, 180., 1200, 1100, 1058, 835, 810, 795, 778, 75., 743. |
| 26 | H | —COOCH₃ | [2,5-dimethylfuran-3-yl] | resin | 3038, 2970, 2935, 2908, 1725, 1615, 156., 1420, 1310, 1292, 1200, 1130, 1022, 810, 782, 763, 745. |
| 27 | H | —COOCH₃ | [5-methylisoxazol-3-yl] | resin | 3030, 2932, 1728, 1640, 1560, 1430, 1135, 1290, 1210, 1188, 810, 779, 745. |

The new active ingredients have a strong fungitoxic action on phytopathogenic fungi, especially from the Phycomycetes class. The new compounds are therefore suitable for instance for combating Phytophthora infestans in tomatoes and potatoes, Phytophthora parasitica in strawberries, Phytophthora cyctorum in apples, Pseudoperonospora cubensis in cucumbers, Pseudoperonospora humuli in hops, Peronospora destructor in onions, Peronospora sparsa in roses, Peronospora tabacina in tobacco, Plasmopara viticola in grapes, Plasmopara halstedii in sunflowers, Sclerospora macrospora in Indian corn, Bremia lactucae in lettuce, Mucor mucedo in fruit, Rhizopus nigricans in beets, Erysiphe graminis in cereals, Uncinula necator in vines, Podosphaera leucotricha in apples, Sphaerotheca fuliginea in roses, and Erysiphe cichoriacearum in cucumbers. The fungicidal agents contain from 0.1 to 95 wt% of active ingredients, preferably from 0.5 to 90%. The application rates depend on the type of effect desired and are from 0.1 to 5 kg of active ingredient per hectare. Some of the active ingredients have curative properties, i.e., the agents may also be applied after the plants have been infected by the pathogen, and success is still ensured. Active ingredient particles less than 5μ in size have a good fungicidal action.

Furthermore, many of the new compounds have a systemic action, which means that visible plant parts may also be protected by a root treatment.

The agents according to the invention may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur; i.e., the fungicidal ction of the combination product is greater than the effect of the individual components added together. The spectrum of action is particularly favorably influenced when the compounds according to the invention are mixed with the following fungicides: manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis-(thiocarbamoyl)-disulfide, N-trichloromethylthiotetrahydrophthalimide, N-trichloromethylphthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)(-5-methyl-5-methoxymethyl-1,3-oxazolidine-2,4-dione.

The following list of fungicides with which the compounds according to the invention may be combined is intended to illustrate and not restrict the combination possibilities.

Examples of fungicides which may be combined with the compounds according to the invention are: dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N'-propylene-bis-dithiocarbamate, and the ammonia complex of zinc N,N-propylene-bis-dithiocarbamate and N,N'-polypropylene-bis-(thiocarbamoyl)-disulfide; nitro derivatives, e.g., dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-n-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)1-1-formylamino-2,2,2-trichloroethane, 2,6-dimethyl-N-tridecyl-morpholine and its salts, and 2,6-dimethyl-N-cyclododecyl-morpholine and its salts, α-(2-chlorophenyl-α-(4-chlorophenyl)-5-pyrimidine-methanol, 1-(4-chlorophenoxy)-3,3-dimethyl-1-(1H-1,2,4-triazol-1-yl)-2-butanone, 1-(4-chloro-phenoxy)-3,3-dimethyl-1-(1H-1,2,4-triazol-1-yl)-2-butanol and α-(2-chlorophenyl)-α-(4-chlorophenyl)-5-pyrimidine-methanol.

The new active ingredients are applied for instance in the form of directly sprayable solutions, powders, suspensions (including high-percentage aqueous, oily or other suspensions or dispersions), emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible. The finer the particle size of the active ingredients, the better is the herbicidal action.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

For the following experiments, the prior art compounds below were employed for comparison purposes: N-trichloromethylthiophthalimide (compound A) N-trichloromethylthiotetrahydrophthalimide (compound B)

zinc-ethylene-1,2-bis-dithiocarbamate (compound C).

EXPERIMENT 1

Fungicidal action on emergence diseases in peas 100 g samples of pea seeds of the "Senator" variety are carefully shaken for about 5 minutes in glass bottles with 300 mg (=0.3 wt%) of seed disinfectant formulations containing (dry basis) 40% of active ingredient. Subsequently, 100 seeds are sown 3 cm deep and 3 to 5 cm apart in seed boxes in a compost naturally and heavily infested with the fungi Pythium sepc., Aphanomyces spec. and Fusarium oxysporum. The boxes are set up in the greenhouse at from 17° to 20° C. The number of healthy pea plants is determined after 21 days.

| Active ingredient | Percentage of healthy plants after 21 days in compost |
|---|---|
| 2 | 86 |
| 10 | 84 |
| 16 | 92 |
| 19 | 90 |
| 20 | 88 |
| 21 | 85 |
| Compound B (comparative agent) | 70 |
| Control (untreated) infested compost | 18 |
| Control (untreated) sterilized compost | 92 |

EXPERIMENT 2

Action on Erysiphe graminis in wheat

Leaves of pot-grown wheat seedlings of the "Jubilar" variety are sprayed with aqueous suspensions consisting of 80% (by weight) of active ingredient and 20% of emulsifier, and dusted, after the sprayed-on layer has dried, with spores of wheat mildew (Erysiphe graminus var. tritici). The plants are then placed in a greenhouse at 20° to 22° C. and 75 to 80% relative humidity. The extent of mildew spread is determined after 10 days.

| Active ingredient | Leaf attack after spraying with liquor containing active ingredient in amount of | | |
|---|---|---|---|
|  | 0.025% | 0.012% | 0.006% |
| 5 | 0 | 2 | 4 |
| 8 | 1 | 1 | 3–4 |
| 12 | 0 | 0 | 0 |
| 16 | 0 | 1 | 3–4 |
| 26 | 1 | 1 | 1 |
| Control (untreated) |  | 5 |  |

0 = no fungus damage, graduated down to
5 = total attack

EXPERIMENT 3

Fungicidal action on Phytophthora infestans in tomatoes

Leaves of tomato plants of the "Grosse Fleischtomate" variety are sprayed with aqueous suspensions containing 0.025 wt% of active ingredient. After the sprayed-on liquor has dried, the leaves are infected with a zoospore suspension of Phytophthora infestans. The plants are then placed in a steam-saturated chamber at from 16° to 18° C. After 5 days, the disease has spread on the untreated but infected plants to such an extent that the fungicidal action of the compounds can be assessed.

| Active ingredient | Leaf attack after spraying with liquor containing 0.025% of active ingredients |
|---|---|
| 4 | 0 |
| 8 | 0 |
| 17 | 1 |
| 20 | 0 |
| 21 | 1–2 |
| 24 | 1 |
| Compound C (comparative agent) | 2–3 |
| Control (untreated) | 5 |

0 = no fungus attack, graduated down to
5 = total attack

EXPERIMENT 4

Action on Plasmopara viticola in grapes

Leaves of potted vines of the Müller-Thurgau variety are sprayed with aqueous suspensions containing 0.025 wt% of the active ingredients. To be able to assess the duration of action of the active ingredients, the plants are placed, after the sprayed-on layer has dried, in the greenhouse for 10 days. Only after this period of time are the leaves infected with a zoospore suspension of Plasmopara viticola. The plants are first placed for 16 hours in a steam-saturated (moist) chamber at 24° C. and then in a greenhouse for 8 days at from 20° to 30° C. To accelerate and intensify the sporangiophore discharge, the plants are then again placed in the moist chamber for 16 hours. The spore sites on the underside of the leaves are then counted.

| Active ingredient | Leaf attack after spraying with liquor containing 0.025% of active ingredient |
|---|---|
| 10 | 0 |
| 21 | 0 |
| Compound A (comparative agent) | 2 |
| Control (untreated) | 5 |

0 = no fungus attack, graduated down to
5 = total attack

Examples of formulations are given below.

I. 90 parts by weight of compound 1 is mixed with 10 parts by weight of N-methyl-α-pyrrolidone. A mixture is obtained which is suitable for application in the form of very fine drops.

II. 20 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

III. 20 parts by weight of compound 3 is dissolved in a mixture consisting of 40 parts by weight of cyclohexanone, 30 parts by weight of isobutanol, and 20 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 80 parts by weight of compound 2 is well mixed with 3 parts by weight of the sodium salt of diisobutyl-naphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in 20,000 parts by weight of water, a spray liquor is obtained.

VI. 3 parts by weight of compound 3 is intimately mixed with 97 parts by weight of particulate kaolin. A dust is obtained containing 3% by weight of the active ingredient.

VII. 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 2 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

IX. 20 parts of compound 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An N-substituted 2-methylnaphthylamide of the formula

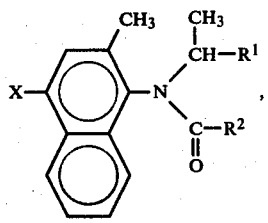

where $R^1$ is

$R^3$ being hydrogen or $C_{1-4}$-alkoxy, and $R^2$ is unsubstituted 3- or 5-isoxazolyl, or mono- or di-substituted 3- or 5-isoxazolyl, wherein the substituents are fluorine, chlorine, bromine, nitro, linear alkyl of 1–4 carbon atoms, methoxy, ethoxy, methylthio, ethylthio, n-propylthio, trichloromethyl, trifluoromethyl, tetrafluoroethoxy, cyano, methoxycarbonyl, acetyl or propionyl, and X is hydrogen, methyl, chlorine or bromine.

2. A compound of the formula I of claim 1, wherein $R^2$ is unsubstituted isoxazolyl.

3. A compound of the formula I of claim 1, wherein $R^2$ is isoxazolyl substituted by 1 or 2 methyl groups.

4. Methyl-N-(3-isoxazolyl-carbonyl)-N-(2'-methyl-1'-naphthyl)-alanate.

* * * * *